United States Patent [19]

Tynan, III

[11] Patent Number: 5,693,524
[45] Date of Patent: Dec. 2, 1997

[54] **ANTICOCCIDIAL COMPOSITION OF UK-61 689 AND *ACTINOMADURA MYCELIUM***

[75] Inventor: Edward J. Tynan, III, Groton, Conn.

[73] Assignee: Pfizer Inc., New York, N.Y.

[21] Appl. No.: 470,306

[22] Filed: Jun. 6, 1995

Related U.S. Application Data

[62] Division of Ser. No. 344,313, Nov. 22, 1994, Pat. No. 5,602,012, which is a continuation of Ser. No. 935,673, Aug. 25, 1992, abandoned, which is a continuation of Ser. No. 506,722, Apr. 9, 1990, abandoned, which is a continuation of Ser. No. 113,563, Oct. 26, 1987, abandoned.

[51] Int. Cl.$^6$ ...................................................... C12N 1/20
[52] U.S. Cl. ........................ 435/252.1; 549/343; 549/75; 549/119; 514/460
[58] Field of Search ..................... 435/75, 119, 252.1; 549/343; 514/460

[56] References Cited

U.S. PATENT DOCUMENTS

| | | | |
|---|---|---|---|
| 4,148,822 | 4/1979 | Celmer et al. | 435/123 X |
| 4,407,946 | 10/1983 | Labeda et al. | 435/252.1 X |
| 4,804,680 | 2/1989 | Goudie et al. | 514/460 |

FOREIGN PATENT DOCUMENTS

| | | | |
|---|---|---|---|
| 169011 | 1/1986 | European Pat. Off. . | |
| 186787 | 8/1987 | Japan | 435/252.1 |

*Primary Examiner*—Irene Marx
*Attorney, Agent, or Firm*—Peter C. Richardson; Gregg C. Benson

[57] ABSTRACT

*Actinomadura roseorufa* mutants characterized by the ability to produce by fermentation UK-61,689, an acidic polycyclic ether anticoccidial antibiotic previously available only by selective acid hydrolysis of UK-58,852; and *Actinomadura roseorufa* having the identifying characteristics of ATCC 53,666, ATCC 53,665, ATCC 53,664 and ATCC 53,674.

6 Claims, No Drawings

ANTICOCCIDIAL COMPOSITION OF UK-61 689 AND *ACTINOMADURA MYCELIUM*

This a division of application Ser. No. 08/344,313, filed Nov. 22, 1994 now U.S. Pat. No. 5,602,012, which is a continuation of application Ser. No. 07/935,673, filed Aug. 25, 1992, now abandoned, which is a continuation of application Ser. No. 07/506,722, filed Apr. 9, 1990, now abandoned, which is a continuation of application Ser. No. 07/113,563, filed Oct. 26, 1987, now abandoned.

BACKGROUND OF THE INVENTION

1. Field of the Invention

This invention relates to a microbiological process for producing UK-61,689, an acidic polycyclic ether anticoccidial antibiotic previously available only by chemical means. More particularly it relates to fermentative production of UK-61,689 by cultivating *Actinomadura roseorufa* having the identifying characteristics of ATCC 53,666; and to *Actinomadura roseorufa* mutants having the identifying characteristics of ATCC 53,665, ATCC 53,664 and ATCC 53,674.

2. Description of Related Art

EP-0169011, published Jan. 22, 1986 describes production of UK-58,852, a polycyclic ether antibiotic produced by cultivation of *Actinomadura roseorufa* Huang sp. nov., ATCC 39,697 in an aqueous nutrient medium under submerged aerobic conditions.

UK-61,689, a monoglycone acidic polycyclic ether has formula (I),

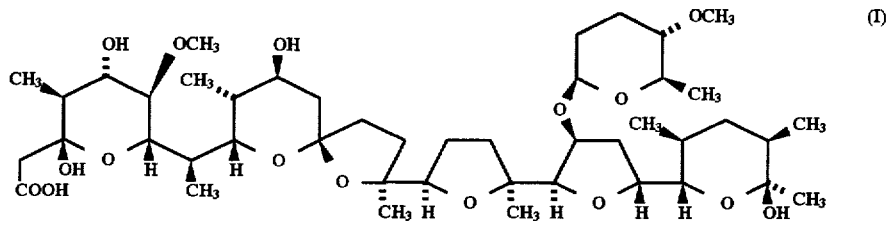

Its preparation by the selective acid hydrolysis of UK-58, 852, a diglycone polycyclic ether having formula (II),

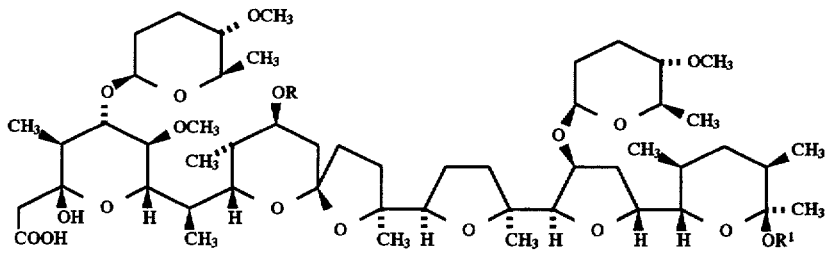

is described in British Patent Application No. 8618844, filed Aug. 1, 1986. The process described therein comprises acid hydrolysis of UK-58,852, preferably using 1:1 equivalents of p-toluenesulfonic acid per equivalent of the sodium salt of UK-58,852 in acetonitrile/water as solvent at room temperature.

The preparation of UK-58,852, itself an effective antibiotic, especially anticoccidial agent, is described in EP application 169011, published Jan. 22, 1986. It is produced by submerged aerobic fermentation in aqueous nutrient media of *Actinomadura roseorufa* Huang sp. nov. ATCC 39,697. Also produced in the fermentation with UK-58,852 are two related minor components, each of which is antibiotically effective in controlling coccidiosis. The two minor components, designated as CP-70,228 and CP-70,828, have formula (II), above, wherein R is H and $R^1$ is $CH_3$; and each of R and $R^1$ is methyl, respectively.

SUMMARY OF THE INVENTION

This invention is concerned with microbiological processes for making UK-61,689, a valuable acidic polycyclic ether antibiotic and potent anticoccidial, which comprises cultivating mutants of *Actinomadura roseorufa* ATCC 53,666 in an aqueous nutrient medium under, preferably submerged, aerobic conditions. It is especially concerned with mutants ATCC 53,674 and 53,665 derived from *Actinomadura roseorufa* ATCC 53,666, which are characterized by their ability to produce UK-61,689 along with UK-58, 852 and to a mutant of ATCC 53,665, which is characterized by its ability to produce 61,689 substantially free of UK-58, 852, said mutant having the identifying characteristics of *Actinomadura roseorufa* ATCC 53,664.

DETAILED DESCRIPTION OF THE INVENTION

The UK-61,689 and UK-58,852 producing microorganisms were obtained by mutation of a new strain of *Actinomadura roseorufa*, designated FD-27684, (ATCC 53,666), isolated from a soil sample collected in Yamae Village, Kamamoto, Japan. N-methyl-N'-nitro-N-nitrosoguanidine (NTG) was used as mutating agent. Single colonies of the treated microorganism were then examined for production of UK-61,689. The general procedure comprised growing ATCC 53,666 in an aqueous nutrient medium under submerged aerobic conditions with shaking at a temperature of 28° C. The choice of medium for the growth stage is not critical. A medium consisting of cerelose (10.0 g), corn starch (5.0 g), corn steep liquor (5.0 g), NZ Amine YTT (5.0 g), (registered trademark for enzymatic digest of casein, Humko Sheffield Chemical Co., Inc.), and cobalt chloride (0.002 g) is suspended in one liter of water, pH adjusted to 7.0 with sodium hydroxide and dispensed (800 ml) to a Fernbach flask. After sterilization by autoclaving, flasks are inoculated with a slant growth suspension or frozen vegetative mycelia, then incubated with agitation on a shaker at about 200 rev/min and a temperature of 28° C. for 8 days. A 50 ml aliquot is then removed, and the mycelia homogenized by a Teflon pestle tissue grinder followed by ultrasonic fragmentation. The fragmented mycelia were then centrifuged, washed free of medium, then resuspended in 50 ml of fresh medium in a 300 ml Erlenmeyer flask, and incubated by shaking at 32° C. for two hours after which the cells were again centrifuged, washed free of medium with sterile water and suspended in 50 ml of tris(hydroxymethyl) aminomethane-malate buffer pH 9.0. Aliquots of this suspension were then treated with the mutagenic agent NTG at concentrations of 750 mcg to 1500 mcg/ml for one hour on a rotary water bath shaker at 250 to 300 rev/min and a temperature of 34° C. After treatment the cells were centrifuged, washed free of the mutagen with sterile water and suspended in flasks of fresh growth medium which were grown by shaking at 32° C. in a cabinet shaker at 200 rev/min. After three days the mycelia outgrowth were homogenized and sonicated. Aliquots of the sonicate were serially diluted, plated onto a solid nutrient medium and the plates incubated at 28° C. until the colony forming units were of sufficient size for transferring to slants. A suitable medium for plates and slants is ATCC Medium No. 172 with N-Z Amine Type A (Humko Sheffield Chemical Co., Inc.) decreased to 1.0 g/l. The inoculated slants were allowed to grow at 28° C. for 10 to 14 days after which time they were ready for testing. This was done by inoculating 300 ml Erlenmeyer flasks containing 25 ml of a suitable medium (one such contains cerelose, 45.0 g; soy flour, 10.0 g; corn steep liquor, 15.0 g; $MnSO_4.H_2O$, 0.1 g; $MgSO_4.7H_2O$, 0.1 g; cobalt chloride, 0.002 g; and calcium carbonate, 3.0 g; one liter of water and the pH of the medium is adjusted to 7.0). After sterilization by autoclaving for 30 minutes at 121° C., the flasks were inoculated with individual slant growth suspensions and incubated by shaking at 28° C. on a New Brunswick shaker for 7 days. The mutant culture FD-28454 (ATCC 53,674) was detected by examining methylisobutyl ketone extracts of harvested whole broths after spraying developed thin-layer chromatographic plates (silica gel) with vanillin reagent and heating at 100° C. for five minutes. The developing system was composed of 9 parts chloroform to 1 part methanol which gave Rf values of ~0.3 for UK-61,689 and ~0.65 for UK-58,852. The mutant culture thus obtained produces a mixture of UK-61,689 and UK-58, 852. The ratio of UK-61,689/UK-58,852 appears to vary somewhat depending upon the conditions of the fermentation. The morphological and cultural characteristics of the thus-obtained mutant are substantially those described herein for A. roseorufa ATCC 53,666. The distinguishing characteristic of this mutant is its ability to produce a mixture of UK-61,689 and UK-58,852 in which UK-61,689 is the predominant product. Cultivation of the mutant and isolation of antibiotic UK-61,689 may be conducted under conditions similar to those employed in previous fermentations yielding polyether antibiotics. See, for example U.S. Pat. No. 4,361,649. Cultivation preferably takes place in aqueous nutrient media under preferably submerged aerobic conditions with agitation at a temperature of 24° C. to 36° C. Nutrient media useful for cultivation include a source of assimilable carbon such as sugars, starches and glycerol; a source of organic nitrogen such as casein, enzymatic digest of casein, soybean meal, cotton seed meal, peanut meal, wheat gluten, soy flour, meat meal and fish meal. A source of growth substances such as grain solubles, fish meal, cotton seed meal and yeast extract as well as mineral salts such as sodium chloride and calcium carbonate and trace elements such as iron, magnesium, copper, zinc, cobalt and manganese may also be utilized with advantageous results. If excessive foaming is encountered during fermentation, antifoam agents such as vegetable oils or silicones may be added to the fermentation medium. Aeration of the medium in vessels for submerged growth is preferably maintained at the rate of ½ to 2 volumes of sterile air per volume of fermentation broth per minute forced into the broth through a sparger. Agitation may be maintained by means of agitators generally familiar to those skilled in the fermentation art. The rate of agitation depends on the type of agitator employed. A shake flask is usually run at 150 to 300 cycles per minute whereas a fermenter is usually run at 300 to 1700 revolutions per minute. Aseptic conditions must, of course, be maintained through the transfer of organism and throughout its growth.

Inoculum for preparation of the antibiotic according to this invention may be obtained by employing growth from a slant of the culture or Roux bottles inoculated with the culture or a thawed mycelia suspension of the culture. A solid medium suitable for initial growth of the organism on slants and Roux bottles is ATCC Medium No. 172. The liquid medium previously mentioned in the mutational study is suitable to prepare the vegetative mycelia prior to freezing. The growth may be used to inoculate either shake flasks or inoculum vessels or the inoculum vessels may be seeded from the shake flasks. Maximum growth in shake flasks is usually reached in 4 to 8 days, whereas inoculum in submerged inoculum vessels will usually be in the most favorable period in 4 to 5 days.

The progress of the antibiotic production during fermentation can be monitored qualitatively by thin-layer chromatography after visualization by spraying with vanillin reagent as previously described or the developed plate can also be overlayed with brain heart infusion agar seeded with *Bacillus subtilis* and incubated at 37° C. for 16 hours to visualize the antibiotics. Thin-layer chromatography is also a useful tool for analyzing the composition of crude and purified materials extracted from the fermentation broth. A HPLC method employing a 10 cm×4.6 mm microbore C-18 column, a 40/200/760 0.01M ammonium carbonate/ acetonitrile/methanol mobile phase, employing a refractive index detector to quantitate the amount of UK-61,689 and co-produced UK-58,852 in fermentation broths.

The antibiotic UK-61,689 produced by the fermentation of the herein described mutants accumulates in the mycelium and in the broth and can be separated and recovered by extracting the harvested whole unfiltered fermentation broth, i.e., the whole broth, with an organic solvent such as chloroform, ethyl acetate, methylisobutyl ketone or butanol at the naturally prevailing pH. Alternatively, to avoid serious emulsion problems the mycelium is separated and both it and the clarified broth extracted individually with an organic solvent. The solvent extracts are then concentrated to a thin syrup and pure UK-61,689 obtained by chromatography.

A typical method of separation and recovery of the antibiotic is as follows: The whole broth from the fermentation of the mutant was extracted with methylisobutyl ketone. Evaporation of the extract in vacuo gave a reddish oil which was dissolved in ethyl acetate and poured onto a column of silica gel. The silica gel column was then eluted with ethyl acetate and the eluates examined by thin-layer chromatography. Fractions containing UK-61,689 were combined and evaporated to dryness. The thus-obtained UK-61,689 can be further purified by crystallization from isopropyl ether.

The UK-61,689 can be recovered from the fermentation in association with the mycelium by evaporation of the whole broth by known methods, including spray drying, or by separation of the mycelium from the broth by filtration or centrifugation. The mycelial products thus obtained comprise UK-61,689 on the surface of the mycelium and in the interstices thereof rendering the mycelium a useful carrier for UK-61,689.

A single colony isolate, designated FD-28474, of the above-described mutant FD-28454 (ATCC 53,674) was itself subjected to mutagenesis by NTG according to the procedure described above for preparation of FD-28454. This procedure gave rise to a further mutant (FD-28499) which exhibited the morphological and cultural characteristics of *Actinomadura roseorufa* ATCC 53,666 and, of course, of the first produced mutant. However, this mutant (FD-28499) differs from mutants FD-28454 and 28474 in that it produces UK-61,689 substantially free (i.e., <1%) of UK-58,852. Mutant FD-28499 is cultivated in the same manner as is the first-described mutant (FD-28454) and the UK-61,689 recovered from the fermentation as previously described.

This last mutant, identified in the culture collection of Pfizer Inc. as FD-28499, mutants FD-28454 and FD-28474, and the starting microorganism, FD-27684, have been deposited on Aug. 28, 1987, Sep. 22, 1987, Aug. 28, 1987 and Aug. 28, 1987, respectively, under the terms of the Budapest Treaty in the American Type Culture Collection, Rockville, Md., a recognized depository affording permanence of the deposits and ready accessibility thereto by the public if a patent is granted on this application. They have been given the designations *Actinomadura roseorufa* ATCC 53,664, ATCC 53,674, ATCC 53,665 and ATCC 53,666, respectively. The deposits are available during pendency of this application to one determined by the Commissioner of the United States Patent and Trademark Office to be entitled thereto under 37 CFR 1.14 and 35 USC 122, and in accordance with foreign patent laws in countries wherein counterparts of this application, or its progeny, are filed. All restrictions on the availability to the public of the microorganisms deposited will be irrevocably removed upon granting of a patent thereon.

Taxonomic investigations of FD-27684, FD-28474 and FD-28499 were carried out by L. H. Huang who provided the following descriptions.

Each of the cultures was planted from a slant into ATCC no. 172 broth and grown for four days at 28° C. on a shaker. It was then centrifuged for 20 minutes, washed three times with sterile distilled water and planted on media commonly used for identification of members of the Actinomycetales.

The cultures were incubated at 28° C. and the results were read at varying times but most commonly were taken at 14 days. The colors are described in common terminology, but exact colors were determined by comparisons with color chips from the *Color Harmony Manual*, Fourth edition. The method of whole-cell amino acid analysis is that described in Becker et al., *Appl. Microbiol.*, 12, 421–423, 1964. Whole-cell sugars were analyzed by the methods described in Lechevalier, *J. Lab. Clin. Med.*, 71, 934–944, 1968; and in Staneck and Roberts, *Appl. Microbiol.* 28, 226–231, 1974. For the purpose of comparison, the type culture of *Actinomadura roseorufa* ATCC 39,697 was used.

Identification media used for the characterization of the cultures and references for their composition are as follows:
1. Tryptone-Yeast Extract Broth—(ISP #1 medium, Difco).
2. Yeast Extract-Malt Extract Agar—(ISP #2 medium, Difco).
3. Oatmeal Agar—(ISP #3 medium, Difco).
4. Inorganic Salts-Starch Agar—(ISP #4 medium, Difco).
5. Glycerol-Asparagine Agar—(ISP #5 medium, Difco).
6. Peptone-Yeast Extract Iron Agar—(ISP #6 medium, Difco).
7. Czapek-Sucrose Agar—S. A. Waksman, The Actinomycetes, Vol. 2, medium no. 1, p. 328, 1961.
8. Glucose-Asparagine Agar—Ibid, medium no. 2, p. 328.
9. Bennett's Agar—Ibid, medium no. 30, p. 331.
10. Emerson's Agar—Ibid, medium no. 28, p. 331.
11. Nutrient Agar—Ibid, medium no. 14, p. 330.
12. Gordon and Smith's Tyrosine Agar—R. E. Gordon and M. M. Smith, *J. Bacteriol.* 69: 147–150, 1955.
13. Casein Agar—Ibid.
14. Calcium Malate Agar—S. A. Waksman, *Bacteriol. Rev.* 21: 1–29, 1957.
15. Gelatin—R. E. Gordon and J. M. Mihm, *J. Bacteriol.* 73: 15–27, 1957.
16. Starch—Ibid.
17. Organic Nitrate Broth—Ibid.
18. Dextrose Nitrate Broth—S. A. Waksman, The Actinomycetes, Vol. 2, medium no. 1, p. 328, 1961, with 3 g dextrose substituted for 30 g sucrose and agar omitted.
19. Potato Carrot Agar—M. P. Lechevalier, *J. Lab. and Clinical Med.* 71: 934–944, 1968, but use only 30 g potatoes, 2.5 g carrots and 20 g agar.
20. 2% Tap Water Agar.
21. Gauze's #1 Mineral Agar—G. F. Gauze et al., Problems in the Classification of Antagtonistic Actinomycetes, English Ed., p. 13, 1957.
22. Gauze's #2 Organic Agar—Ibid.
23. Skim Milk—Difco.
24. Cellulose utilization—
    a) H. L. Jensen, Proc. Linn. Soc. N.S.W. 55: 231–248, 1930.
    b) M. Levine and H. W. Schoenlein, A Compilation of Culture Media, medium no. 2511, 1930.
25. Utilization of Organic Acids—R. E. Gordon et al., *Int. J. Syst. Bacteriol.* 24: 54–63, 1974.
26. Acid Production from Carbohydrates—Ibid.
27. Hydrolysis of Hippurate and Esculin—Ibid.
28. Decomposition of Adenine, Hypoxanthine, Xanthine, and Urea—Ibid.
29. Resistance to Lysozyme—Ibid.
30. Carbohydrate Utilization—C-2 Medium, H. Nonomura and Y. Ohara, *J. Ferment. Technol.* 49: 887–894, 1971.
31. Temperature Range—ATCC medium 172 in ATCC Culture Collection Catalogue, 15th ed., p. 608, 1982.

A Description of Culture FD-27684

Yeast Extract-Malt Extract Agar—Growth good, pink-red to red (6 1/2ia, 7ia; 6ia), raised, wrinkled, with white aerial mycelium; reverse red (7ia); no soluble pigment.

Oatmeal Agar—Growth moderate, cream (2ca), slightly raised, smooth, or appearing as isolated colonies; aerial mycelium none to sparse, white; reverse cream (2ca); no soluble pigment.

Inorganic Salts-Starch Agar—Growth poor to moderate, colorless to cream (2ca), thin, smooth; aerial mycelium none to sparse, white; reverse same as surface; no soluble pigment.

Glycerol-Asparagine Agar—Growth poor to moderate, cream (2ca), with pink to red dots (6ea, 6 1/2ga); aerial mycelium none to sparse, white; reverse colorless to cream (2ca), with red dots; no soluble pigment.

Czapek-Sucrose Agar—Growth poor to moderate, cream (2ca), with pink to red dots (5ea, 6 1/2ia); aerial mycelium none to sparse, white; reverse colorless to cream (2ca); no soluble pigment.

Glucose-Asparagine Agar—Growth moderate to good, pink to red (6 1/2ga, 6 1/2na), raised; smooth, granular to wrinkled; aerial mycelium white to pale pink (6ea); reverse red (6 1/2ga, 6 1/2ia); soluble pigment pale yellowish (3ca).

Gordon and Smith's Tyrosine Agar—Growth moderate to good, pink-orange (5ea), moderately raised, wrinkled; aerial mycelium none to sparse, white; reverse same as surface; soluble pigment yellowish (21c).

Calcium Malate Agar—Growth scant, colorless, thin, smooth, no aerial mycelium; reverse colorless; no soluble pigment.

Casein Agar—Growth moderate to good, pink-orange to orange (4ia, 5ia), moderately raised, wrinkled, no aerial mycelium; reverse yellowish to pale pink (3ga, 5ea); with brown (31c) soluble pigment.

Bennett's Agar—Growth good, red to dark red (6 1/2ne, 6 1/2ng), raised, wrinkled; aerial mycelium white to pink (6ea); reverse red (6 1/21c); with brown (3ne) soluble pigment.

Emerson's Agar—Growth good to excellent, orange (51a, 5na), raised, wrinkled, with white aerial mycelium; reverse orange (5ic); no soluble pigment.

Nutrient Agar—Growth moderate, pale orange (5ea, 5ga), slightly raised, smooth, or appearing as isolated colonies, no aerial mycelium; reverse pale orange (5ga); no soluble pigment.

Gelatin Agar—Growth moderate to good, pale orange (4ga), moderately raised, smooth to wrinkled; aerial mycelium sparse, white; reverse pale orange (4ga); no soluble pigment.

Starch Agar—Growth moderate to good, pale orange (5ga), moderately raised, smooth to wrinkled; aerial mycelium sparse, white; reverse same as surface; no soluble pigment.

Potato Carrot Agar—Growth poor to moderate, cream to pale pink (2ca, 4ca), thin to slightly raised; aerial mycelium sparse, white; reverse cream to pale pink (4ca); no soluble pigment.

Tap Water Agar—Growth poor, colorless to cream (1 1/2ca), thin, smooth; aerial mycelium sparse, white; reverse same as surface; no soluble pigment.

Gauze's Mineral Medium 1—Growth moderate, pink to red (5ca, 61a), with red dots (61c), slightly raised, smooth; aerial mycelium none to sparse, white; reverse same as surface; no soluble pigment.

Gauze's Organic Medium 2—Growth moderate to good, pink-orange (5ga), moderately raised, slightly wrinkled; aerial mycelium sparse, white; reverse same as surface; no soluble pigment.

Morphological Properties—After seven weeks of incubation, no spores were found on any of the media used. On potato carrot agar, however, hyphal swellings were produced terminally, laterally or intercalarily; and were single and smooth. They were globose, oval to elliptical, and measured 1.2–2.5 m diam. or 1.2–2.2× 0.9–1.8 m. The similar structures were also found on yeast extract-malt extract agar, oatmeal agar, tap water agar, gelatin agar, Czapek-sucrose agar, and Gauze's mineral medium 1.

Biochemical Properties—Melanin not produced; hydrogen sulfide not produced; gelatin liquefied; starch not hydrolyzed; nitrate reduced to nitrite; slight growth on Jensen's cellulose broth but no growth on Levine and Schoenlein's cellulose broth; no disintegration on both cellulose broths; coagulation and peptonization on milk; digestion of calcium malage negative; tyrosine digestion positive; casein digestion positive.

Carbohydrate utilization: glucose, rhamnose, and sucrose utilized; arabinose, fructose, inositol, mannitol, raffinose, and xylose not utilized.

The positive tests included: utilization of acetate, propionate, and pyruvate; acid production from glucose, rhamnose, maltose, and trehalose.

The following tests were negative: decomposition of adenine, xanthine, hypoxanthine, and urea; hydrolysis of esculin and hippurate; resistance to lysozyme; utilization of benzoate, citrate, dextrin, lactate, malate, mucate, oxalate, phenol, and succinate; acid production from arabinose, fructose, inositol, mannitol, raffinose, sucrose, xylose, adonitol, cellobiose, dulcitol, erythritol, galactose, glycerol, lactose, mannose, melezitose, malibiose, alpha-methyl-D-glucoside, ribose, salicin, sorbitol, sorbose, and starch.

Whole-cell Analysis—The whole-cell hydrolysates contain mesodiaminopimelic acid, galactose, glucose, madurose, ribose, and rhamnose.

Temperature Relations—

| 21° C. | 28° C. | 37° C. | 45° C. |
|---|---|---|---|
| Moderate Growth | Good Growth | Moderate Growth | No Growth |

Culture FD-27684 is characterized by the inability to produce melanin; the pink, pink-orange, orange to red substrate mycelium; and the presence of meso-diaminopimelic acid and madurose as whole-cell components. Despite a long incubation period of up to seven weeks, the culture failed to produce spores although hyphal swellings were produced on some media. It is assignable to the genus Actinomadura.

Culture FD-27684 was similar to *Actinomadura roseorufa* Huang ATCC 39,697 (see European Patent Application 169 001) in most of the cultural characteristics and almost all of the biochemical properties. On gelatin agar and starch agar, colonies of FD-27684 were pale orange rather than pale cream. On tyrosine agar and Emerson's agar, they showed some tint of orange rather than brown. Culture FD-27684, unlike *A. roseorufa*, coagulated milk. These differences were minor and hence culture FD-27684 is considered as a new strain of *A. roseorufa*.

Compared with the parent culture FD-27684, mutant FD-28474 produced less aerial mycelium on yeast extract-malt extract agar, Bennett's agar, Gauze's organic medium 2, gelatin agar, and starch agar. Colonies of the mutant were cream rather than orange on Emerson's agar and were pale pink rather than cream to pale pink on potato carrot agar. The mutant, unlike its parent, produced hydrogen sulfide. All of the other cultural characteristics and biochemical properties were identical. Thus, mutant FD-28474 is considered as a new strain of *Actinomadura roseorufa*.

Compared with culture FD-28474 from which it was derived, mutant FD-28499 shared almost all of the cultural characteristics and all of the biochemical properties. The mutant differed from culture FD-28474 only in the dark brown rather than dark red colonies on yeast extract-malt extract agar and in the presence of some pink dots on Gauze's organic medium 2. Thus, mutant FD-28499 is considered as a new strain of *Actinomadura roseorufa*.

FD-28454 was not subjected to taxonomic study. However, since it was derived from a strain of *Actinomadura roseorufa*, and by mutation produced a strain of *Actinoma-*

*dura roseorufa*, it is considered to be a strain of *Actinomadura roseorufa*.

Antibiotic UK-61,689 exhibits inhibitory action against the growth of a number of Gram-positive microorganisms. In Table I, below, the results of in vitro tests are summarized. For this test each organism is inoculated in a series of test tubes containing nutrient medium and varying concentrations of Antibiotic UK-61,689 to determine the minimal concentration of the compound in g/ml which inhibits the growth of the organism over a period of 24 hours (MIC).

TABLE I

| Antibacterial Activity | | |
|---|---|---|
| Organism | Strain No. | MIC µg/ml |
| *Clostridium perfringens* | 10A006 | 50 |
| | 10A009 | 12.5 |
| *Actinomyces pyogenes* | 14D002 | 50 |
| | 14D008 | 50 |
| | 14D011 | 50 |
| *Treponema hyodysenteriae* | 94A001 | 3.12 |
| | 94A002 | 3.12 |
| | 94A007 | 1.56 |
| | 94A008 | 1.56 |

Efficacy data for UK-61,689 and its salts against coccidial infections in chickens were obtained in the following fashion. Groups of 3–5 ten-day-old, pathogen-free white leghorn cockerel chicks were fed a mash diet containing UK-61,689 or its sodium and/or potassium salt uniformly dispersed therein. After being on this ration for 24 hours, each chick was inoculated per os with oocysts of the particular species of Eimeria being tested. Other groups of 3–5 ten-day-old chicks were fed a similar mash diet without Antibiotic UK-61,689 or its salts. They were also infected after 24 hours and served as infected controls. Yet another group of 3–5 ten-day-old chicks were fed the same mash diet without antibiotic UK-61,689 and were not infected with coccidia. These served as normal controls. The results of treatment were evaluated after five days in the case of *E. acervulina*, and six days for all other challenges.

The criteria used to measure anticoccidial activity consisted of lesion scores of 0 to 4 for *E. tenella* after J. E. Lynch, "A New Method for the Primary Evaluation of Anticoccidial Activity," Am. J. Vet. Res., 22, 324–326, 1961; and 0 to 3 for the other species based on modification of the scoring system devised by J. Johnson and W. H. Reid, "Anticoccidial Drugs. Lesion Scoring Techniques in Battery and Floor Pen Experiments in Chicks," Exp Parasit., 28, 30–36, 1970. A constant ratio was established by dividing the lesion score of each treated group by the lesion score of the infected control.

UK-61,689 and its cationic salts exhibit excellent activity against coccidial infections in poultry. When incorporated into the diet of chickens at levels of 15 to 120 ppm, these compounds are effective in controlling infections due to *Eimeria tenella, E. acervulina, E. maxima, E. brunetti* and *E. necatrix*.

For use in the treatment of coccidiosis in poultry the compound of this invention is administered orally in a suitable carrier. Conveniently, the medication is simply carried in the drinking water or in the poultry feed, so that a therapeutic dosage of the agent is ingested with the daily water or poultry ration. The agent can be directly metered into drinking water, preferably in the form of a liquid, water-soluble concentrate (such as aqueous solution of a water soluble salt) or added directly to the feed, as such, or in the form of a premix or concentrate. A premix or concentrate of therapeutic agent in a carrier is commonly employed for the inclusion of the agent in the feed. Suitable carriers are liquid or solid, as desired, such as water, various meals; for example, soybean oil meal, linseed oil meal, corncob meal, and mineral mixes such as are commonly employed in poultry feeds. A particularly effective carrier is the poultry feed itself; that is, a small portion of poultry feed. Further, the mycelium can be used as the carrier. The carrier facilitates uniform distribution of the active materials in the finished feed with which the premix is blended. This is important because only small proportions of the present potent agents are required. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with proteinaceous carrier such as soybean oil meal and other meals, as described above, to produce concentrated supplements which are suitable for direct feeding to poultry. In such instances, the poultry are permitted to consume the usual diet. Alternatively, such concentrated supplements may be added directly to the poultry feed to produce a nutritionally balanced, finished feed containing a therapeutically effective level of the compound of this invention. The mixtures are thoroughly blended by standard procedures, such as in a twin shell blender, to ensure homogeneity.

It will, of course, be obvious to those skilled in the art that the use levels of the compound described herein will vary under different circumstances. Continuous low-level medication, during the growing period; that is, during the first 6 to 12 weeks for chickens, is an effective prophylactic measure. In the treatment of established infections, higher levels may be necessary to overcome the infection. The use level in feed will generally be in the range of 15 to 120 ppm. When administered in drinking water, the level which will be that which will provide the same daily dose of medication, i.e., 15 to 120 ppm, factored by the weight ratio of the average daily consumption of feed to the average daily consumption of water.

The present invention is illustrated by the following examples. However, it should be understood that the invention is not limited to the specific details of these examples.

EXAMPLE 1

A. Preparation of Inoculum

A sterile aqueous medium having the following composition was prepared.

| Ingredient | Grams/liter |
|---|---|
| Cerelose | 10.0 |
| Corn starch | 5.0 |
| Corn steep liquor | 5.0 |
| NZ Amine YTT* | 5.0 |
| Cobalt chloride | 0.002 |

*Registered trademark for enzymatic digest of casein, Humko Sheffield Chemical Co. Inc.)

After the pH was adjusted to 7.0, the medium was dispensed (800 ml) into 2800 ml Fernbach flasks, cotton plugged/paper capped and sterilized by autoclaving for 60 minutes at 121° C. (15 p.s.i.). After cooling, the medium was inoculated with a vegetative cell suspension from a slant of FD-28454

(ATCC 53,674). The flasks were shaken at 28° C. on a rotary shaker having a displacement of 1½ to 2½ inches and 150 to 200 cycles per minute for 6 days.

B. Fermentation and Isolation of UK-61,689

A Fernbach flask containing 800 ml of the grown culture was used to inoculate a 14-liter fermentation vessel containing 8 liters of sterile medium of the following composition to which 4 ml of silicone anti-foaming agent had been added:

| Ingredient | Grams/liter |
| --- | --- |
| Cerelose | 45.0 |
| Soy flour | 10.0 |
| Corn steep liquor | 15.0 |
| Blood meal | 5.0 |
| Corn flour | 5.0 |
| $MnSO_4.H_2O$ | 0.1 |
| $MgSO_4.7H_2O$ | 0.1 |
| $COCl_2.6H_2O$ | 0.002 |
| Calcium carbonate | 3.0 |
| pH adjusted to 6.9–7.0 | |

Fermentation was carried out at 30° C. with stirring at 500 revolutions per minute and aeration at 0.75 volume air per volume of broth per minute until substantial activity was produced. The UK-61,689/UK-58,852 in the broth and recovery streams was visualized by using silica gel thin layer chromatography plates developed with a system consisting of 9:1 chloroform:methanol. The plates were sprayed with vanillin reagent (6 g vanillin in 100 ml ethanol and 3% concentrated $H_2SO_4$) and heated at 100° C. for 5 minutes. UK-61,689 appears as a reddish-blue spot. Alternatively, the plate was overlayed with agar seeded with *B. subtilis*, to which 0.4 ml of a 5% solution of 2,3,5-triphenyl-2H-tetrazolium chloride had been added, and incubated at 37° C. for 16 hours to visualize the antibiotic as a colorless area against a red background.

The whole broth was then extracted with methylisobutyl ketone and the solvent concentrated to yield 14.4 g residue. This material was chromatographed on a 6×100 cm column packed with column grade silica gel G (70–230 mesh, Woelm) in ethyl acetate. The column was developed with ethyl acetate at a flow rate of ~20 ml/min. Fractions of 10 ml each were taken.

The fractions were examined by thin-layer chromatography on Analtech silica gel GF plates developed with 9 $CHCl_3$:1 MEOH and visualized by spraying with vanillin reagent and heating.

The fractions containing antibiotic UK-61,689 were combined (total volume approximately 200 ml) and stirred with ~2 g Darco G60 for 15 minutes. After removing the carbon by filtration, the filtrate (ethyl acetate) was washed with dibasic sodium phosphate, 5% buffer adjusted to pH 10.0 with 1N NaOH. After separation, the ethyl acetate layer was dried over anhydrous sodium sulfate and then evaporated under vacuum. The viscous oil remaining after evaporation was dissolved in a small volume of heptane whereupon crystallization occurred. The crystals were collected by filtration and dried under vacuum yielding 1.4 g of antibiotic UK-61,689 as the sodium salt; m.p. 167° C.; $C^{13}$NMR ($CDCl_3$) in ppm: 179.16, 107.54, 103.21, 97.80, 97.01, 87.02, 84.65, 84.28, 82.39, 82.10, 80.92, 80.28, 79.96, 77.62, 77.11, 76.60, 74.91, 74.65, 73.15, 70.19, 67.74, 66.94, 59.07, 56.84, 45.49, 39.92, 39.00, 36.55, 33.88, 33.79, 33.63, 33.51, 33.21, 32.51, 32.33, 30.63, 27.64, 26.98, 26.91, 26.16, 23.25, 18.43, 17.53, 17.00, 12.13, 11.05, 10.47.

The fractions containing UK-58,852 are combined, treated with ~42 g Darco G60 as above, then concentrated. The residue is suspended in hexane and batch treated with silica gel on a filter funnel. The absorbant is washed with hexane, then eluted with chloroform and ethyl acetate. The ethyl acetate fraction is concentrated, the residue rechromatographed on silica and the product crystallized from heptane to give antibiotic UK-58,852 as a white solid.

EXAMPLE 2

The procedure of Example 1 was followed but using FD-28499 (ATCC 53,664) in place of FD-28454 (ATCC 53,674). HPLC of the methyl isobutyl ketone extract of the whole broth afforded UK-61,689 substantially free (<1%) of UK-58,852. Its TLC behavior was identical to that reported in Example 1 for UK-61,689.

The acid form of UK-61,689 is prepared by stirring a chloroform solution of the sodium salt with an equal volume of water and lowering the pH to 3.0 with phosphoric acid. The phases are then separated, and the chloroform evaporated under vacuum to give Antibiotic UK-61,689 as the free acid.

EXAMPLE 3

FD-28474 (ATCC 53,665) was fermented according to the procedure of Example 1 except the fermentation medium contained no corn steep liquor or blood meal. The whole broths from four such fermentations were combined and filtered. The filtrate and mycelium were each extracted with methyl isobutyl ketone (3×200 ml). The extracts were combined and concentrated under reduced pressure to an oil (18.5 g). The oil was taken up in acetone (200 ml) and the solution divided into two equal volumes (I and II).

The pH of volume I was adjusted to 12 by addition of aqueous sodium hydroxide (20%). The alkaline solution was then filtered and concentrated to an oil under reduced pressure. Actone (10 ml), heptane (79 ml) and water (39 ml) were added to the oil to provide dark brown crystals. Repulping of the crystals in heptane gave light brown crystals (2 g) comprising 75% UK-61,689 and 5% UK-58,852 by HPLC assay.

Volume 2 was concentrated to an oil under reduced pressure and the oil dissolved in ethyl acetate (100 ml). It was then subjected to column chromatography over silica gel (500 g) using ethyl acetate as eluting agent. The UK-61,689 rich fractions were combined and concentrated to an oil. The oil was taken up in acetone (10 ml)-heptane (110 ml) and the resulting crystals of UK-61,689 filtered and dried (1.2 g). The UK-58,852 was not recovered.

I claim:

1. An anticoccidial composition comprising UK-61,689 in association with mycelium produced in a process which comprises fermenting *Actinomadura roseorufa* which produces compound UK-61,689 in an aqueous nutrient medium containing assimilable sources of carbon, nitrogen and inorganic salts under submerged aerobic fermentation conditions until a recoverable amount of compound UK-61,689 accumulates in the whole broth; and recovering compound UK-61,689 in association with mycelium of said *Actinomadura roseorufa*.

2. An anticoccidial composition comprising UK-61,689 in association with mycelium produced in a process which comprises fermenting, in an aqueous medium containing assimilable sources of carbon, nitrogen and inorganic salts under submerged aerobic conditions, a strain belonging to the genus Actinomadura, wherein said strain is a mutant obtained by mutating a UK-58,852 producing strain of *Actinomadura roseorufa* and which mutant produces UK-61,689 upon cultivation in said aqueous nutrient medium until a recoverable amount of compound UK-61,689 accumulates in the whole broth; and recovering compound UK-61,689 in association with mycelium of said Actinomadura.

3. An anticoccidial composition according to claim 1 wherein said *Actinomadura roseorufa* has all of the identifying characteristics of ATCC 53,665 or ATCC 53,674.

4. An anticoccidial composition according to claim 1 wherein said *Actinomadura roseorufa* has all of the identifying characteristics of ATCC 53,664.

5. An anticoccidial composition according to claim 3 wherein said *Actinomadura roseorufa* is *Actinomadura roseorufa* ATCC 53,665 or ATCC 53,674.

6. An anticoccidial composition according to claim 4 wherein said *Actinomadura roseorufa* is *Actinomadura roseorufa* ATCC 53,664.

* * * * *

UNITED STATES PATENT AND TRADEMARK OFFICE
CERTIFICATE OF CORRECTION

PATENT NO. : 5,693,524

DATED : December 2, 1997

INVENTOR(S) : Edward J. Tynan, III

It is certified that error appears in the above-identified patent and that said Letters Patent is hereby corrected as shown below:

Column 1, line 45, insert, after "formula II", --wherein R and $R^1$ are H--; and Column 12, line 2, "~42" should read ---~2--.

Signed and Sealed this

Twenty-fourth Day of August, 1999

*Attest:*

Q. TODD DICKINSON

*Attesting Officer*      *Acting Commissioner of Patents and Trademarks*